United States Patent [19]
Narciso, Jr.

[11] Patent Number: 5,419,760
[45] Date of Patent: May 30, 1995

[54] MEDICAMENT DISPENSING STENT FOR PREVENTION OF RESTENOSIS OF A BLOOD VESSEL

[75] Inventor: Hugh L. Narciso, Jr., Santa Barbara

[73] Assignee: PDT Systems, Inc., Santa Barbara, Calif.

[21] Appl. No.: 320,779

[22] Filed: Oct. 11, 1994

Related U.S. Application Data

[63] Continuation of Ser. No. 2,209, Jan. 8, 1993, abandoned.

[51] Int. Cl.⁶ .............................................. A61B 6/00
[52] U.S. Cl. ...................................... 604/8; 606/154; 606/194
[58] Field of Search ........................ 604/8, 9, 10, 21; 606/154, 194; 623/1

[56] References Cited

U.S. PATENT DOCUMENTS

| | | | |
|---|---|---|---|
| 3,914,802 | 10/1975 | Reick | 623/1 |
| 4,512,762 | 4/1985 | Spears | 604/21 |
| 5,019,075 | 5/1991 | Spears et al. | 604/194 X |
| 5,019,090 | 5/1991 | Pinchuk | 606/194 |
| 5,064,057 | 11/1991 | Iwatsuki et al. | 606/154 |
| 5,085,966 | 2/1992 | Suzuki et al. | |
| 5,112,718 | 5/1992 | Kato et al. | |
| 5,197,977 | 3/1993 | Hoffman, Jr. et al. | 623/1 |
| 5,234,456 | 8/1993 | Silvestrini | 606/194 |
| 5,236,447 | 8/1993 | Kubo et al. | 623/1 |

*Primary Examiner*—Sam Rimell
*Attorney, Agent, or Firm*—Michael G. Petit

[57] ABSTRACT

Following recanalization of a stenotic blood vessel, a photosensitizer is administered by means of a vasoabsorbable stent to maintain the photosensitizer concentration level in the atheromatous plaque and smooth muscle cells in the vicinity of the lesion for a period of 5–18 days, the period in which cell proliferation can occur. The Vaso-Absorbable Stent (VAST) is described along with the method for its use in Photoatherolytic (PAL) Therapy. The VAST device is used post cardiovascular intervention to: a) deliver a series of drugs to prevent cell proliferation leading to restenosis; and, (b) maintain the patency of the treated vessel and prevent elastic recoil of the vessel by providing support for the vessel wall; and c) deliver and maintain a level of photosensitizer to the treatment site which inhibits smooth muscle cell proliferation and, when activated by light energy, induces cell lysis. The photosensitizer inhibits smooth muscle cell proliferation and, thus, minimizes or eliminates the possibility of re-stenosis. The photosensitizer is then illuminated at the end of this period, thereby lysing the atheromatous plaque and smooth muscles.

1 Claim, 5 Drawing Sheets

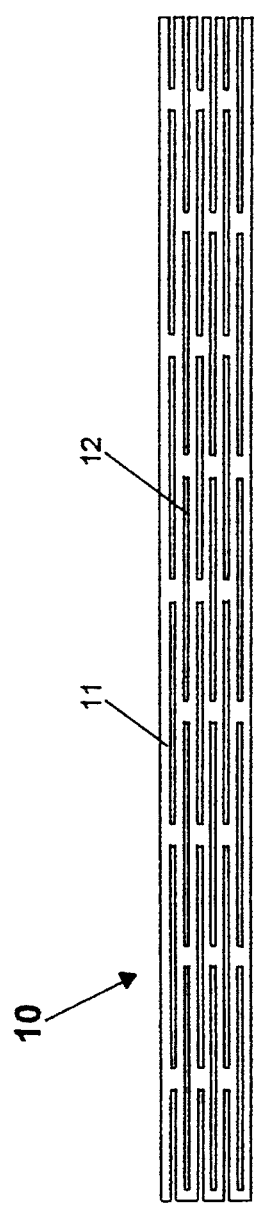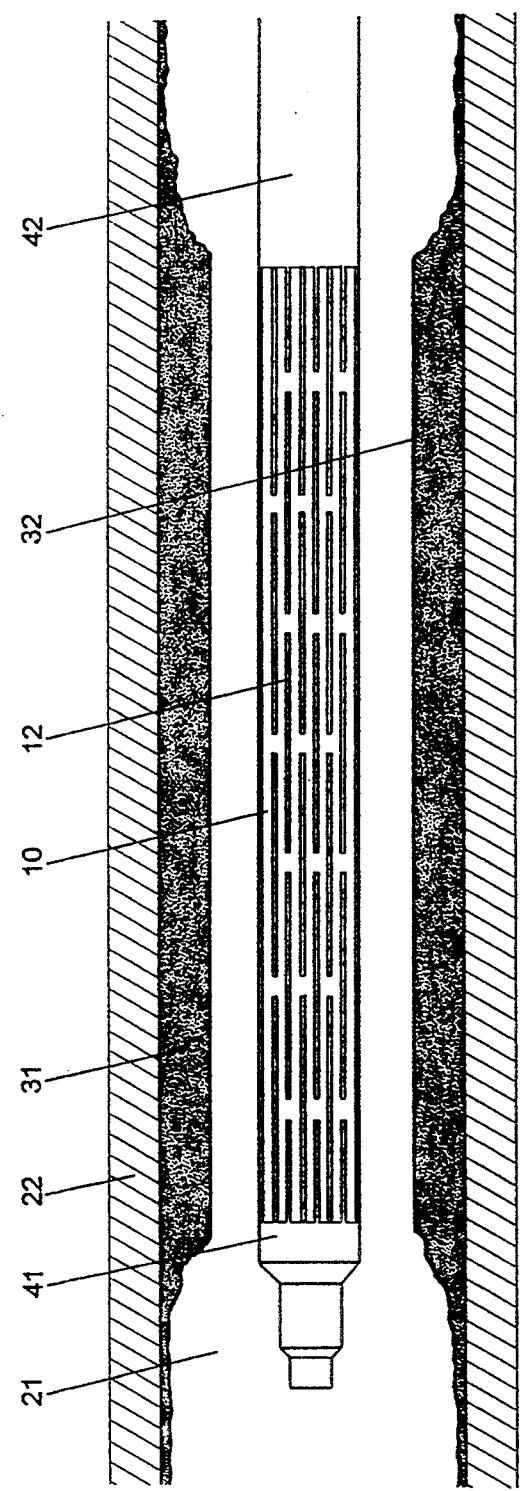
Figure 1
Figure 4

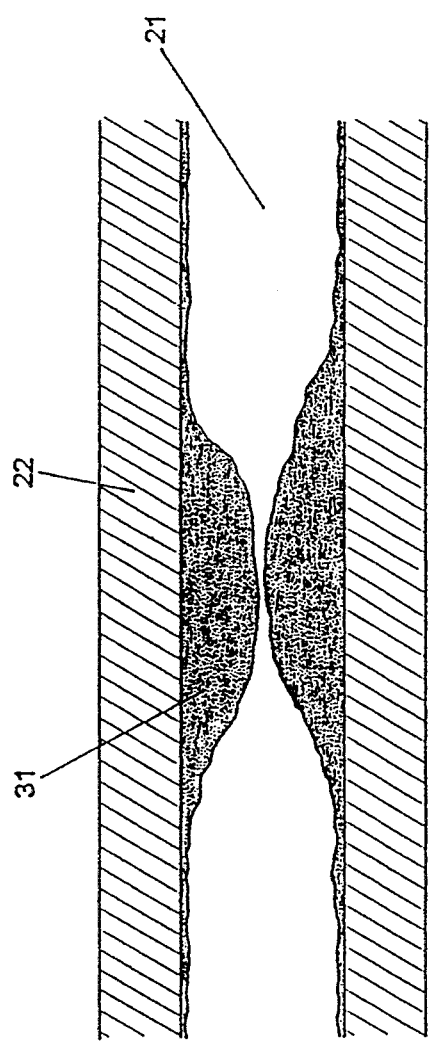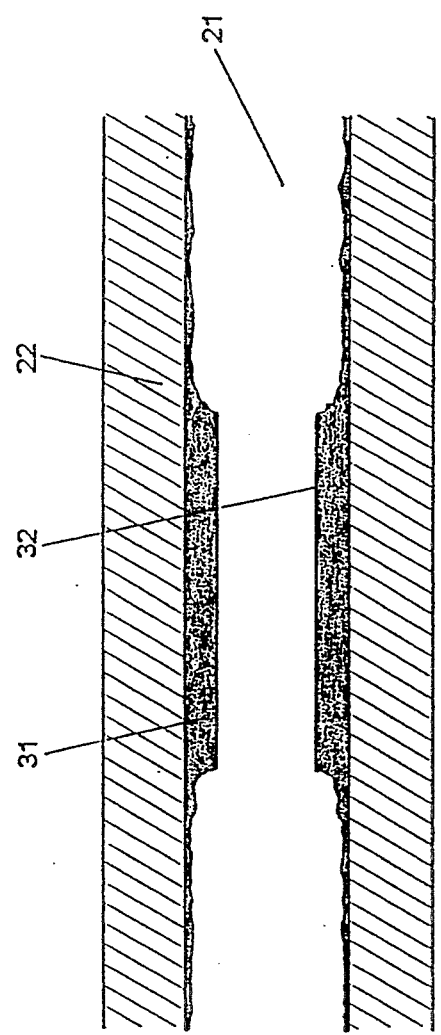

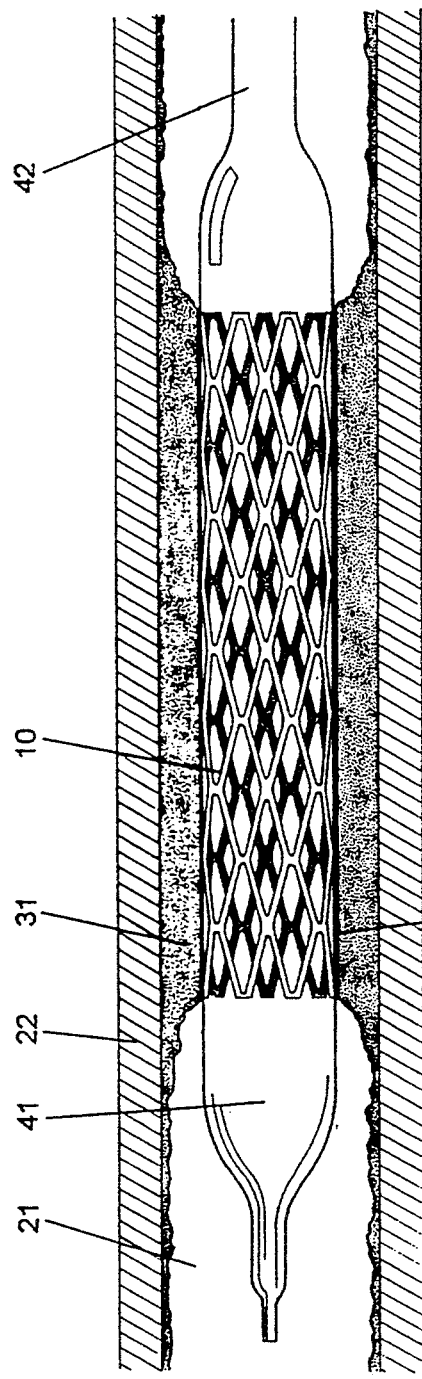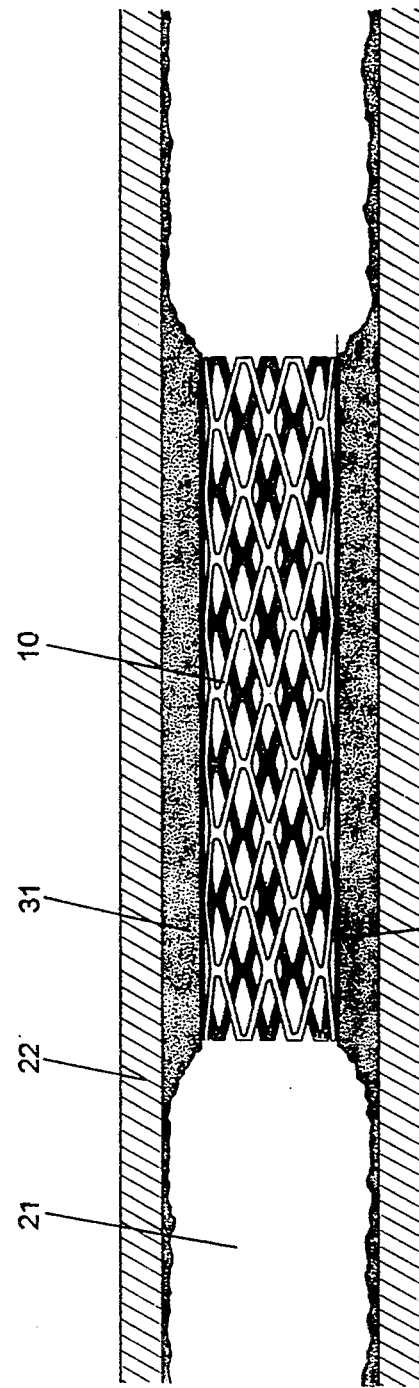
Figure 5
Figure 6

MEDICAMENT DISPENSING STENT FOR PREVENTION OF RESTENOSIS OF A BLOOD VESSEL

CROSS REFERENCE TO RELATED APPLICATIONS

This is a continuation of application Ser. No. 08/002,209; filed Jan. 8, 1993, now abandoned.

BACKGROUND OF THE INVENTION

1. Field of the Invention

The present invention relates to the treatment of atherosclerosis through adjunctive photodynamic therapy generally, and more particularly to the prevention of restenosis following atherectomy or angioplasty.

2. Prior Art

Atherosclerosis is a cardiovascular disease in which deposits of plaques (atheromas) containing cholesterol, lipid material, foam cells, lipophages and proliferating smooth muscle cells are within the intima and media of large to small diameter arteries such as the aorta and the iliac, femoral, coronary and cerebral arteries. The resultant stenosis causes reduction in blood flow.

Attempts to treat atherosclerosis have included bypass surgery wherein the diseased vascular segments are augmented by prosthetic or natural grafts. This procedure requires general anesthesia and a substantial healing period after surgery and, thus, is generally limited to cases of severe coronary artery disease.

Other approaches for the recanalization of stenotic vessels include percutaneous transluminal coronary angioplasty (PTCA), atherectomy, stenting and newer modalities of cardiovascular intervention including laser angioplasty. The word "recanalization", as used herein, means a procedure for increasing blood flow through the occluded vessel by angioplasty, including dilation or ablation or removal of occlusive material. The primary drawbacks of these methods has been restenosis. Studies have shown that restenosis, or the re-narrowing, of the internal lumen of an artery subsequent to such recanalization occurs in about 25-50% of cases where such primary treatment is performed. The result of restenosis is the requirement for an additional interventional or surgical procedure.

Various mechanisms can cause re-stenosis. One mechanism is rapid smooth muscle cell (SMC) proliferation at the lesion site. Smooth muscle cell proliferation is believed to occur immediately or at any time up to several hours after vessel wall injury that results from primary atherosclerotic treatment such as angioplasty. This proliferation continues for about 5-18 days depending on the individual. The cause of this rapid smooth muscle cell proliferation is believed to involve the release of various growth factors in response to the vessel wall injury. Specifically, after such vessel wall injury, some smooth muscle cells migrate to the intima where they are affected by the blood elements with which they come in contact, especially platelets and lipoproteins. Platelets contain a factor that stimulates smooth muscle cell proliferation and migration, which can result in re-stenosis.

March, et al., in U.S. Pat. No. 5,116,864 provides a method for preventing re-stenosis in a patient undergoing vascular recanalization. The method comprises the systemic administration of a photoactivatable psoralen compound, preferably by an oral route, to achieve serum levels around 1 $\mu$M. Alternatively, the psoralen may be delivered to the tissue by intra-arterial injection through a catheter. Following psoralen administration, the atheroma is illuminated with ultraviolet radiation until recanalization is complete. This is where March, et al.'s treatment ends.

Other drugs are used to prevent restenosis. One such drug is heparin. Heparin is an anticoagulant which when delivered systemically severely reduces the ability of the body to form blood clots. Devices for preventing restenosis such as implantable stents require massive doses of heparin which requires the patient to remain hospitalized for a long period of time.

Stents are presently being investigated as a treatment for cardiovascular disease, Early results indicate that stents have a similar rate of restenosis when compared to conventional interventions with the added complication of abrupt closure of the vessel. Stents have also been used as a "bail out" device to maintain the patency of a collapsing artery until another corrective medical procedure can be performed. Stents are composed of many materials including stainless steel, biodegradable polymers, collagen, gelatin, etc.

Local drug delivery devices such as suppositories and dermal patches have been used as indwelling devices. Indwelling devices to treat cardiovascular disease through delivery of local drugs are not clinically available.

Accordingly, there is a need to address the problem of smooth muscle cell proliferation in the treatment of atherosclerosis to minimize or eliminate the occurrence of restenosis.

SUMMARY OF THE INVENTION

The present invention is directed to a method for treating vascular disease that avoids the problems and disadvantages of the prior art. The invention accomplishes this goal by providing a bioabsorbable stent which releases a medicament. As used herein, the term "bioabsorbable," when used in reference to a stent, or a portion thereof, means that the portion of the stent described as bioabsorbable disintegrates following implantation within a body, normally within 2-3 months. The medicament blocks the growth factor binding sites on the atherosclerotic smooth muscle cells (SMC) injured during the recanalization until growth factor is no longer released from the platelets in the vicinity of the injured cells. In this way, smooth muscle cell proliferation in the vicinity of the lesion site is inhibited, thereby minimizing or eliminating the occurrence of restenosis.

The VAST device is used post recanalization to: a) deliver a photosensitive medicament which blocks the chain of events linked to restenosis along with delivering other medicaments to prevent events linked to restenosis such as thrombosis and the formation of an intravascular matrix of collagen and fibrin; b) maintain the patency of the treated artery and prevent elastic recoil of the artery by adding structure and support to the vessel wall; and c) deliver and maintain a level of photosensitizer to the treatment site which inhibits smooth muscle cell proliferation and, when activated by light energy, induces cell lysis.

In the preferred embodiment, the blocking step is accomplished by introducing a photosensitizing agent in the region of the vessel subject to the recanalization such that the agent accumulates in the atheromatous plaque and injured smooth muscle cells. The photosensitizer, accumulated in the atheromatous plaque and smooth muscle cells, blocks the smooth muscle sell growth factor binding sites to inhibit smooth muscle cell proliferation. The photosensitizer is slowly released as the drug-laden bioabsorbable wall of the VAST slowly disintegrates over a period of about 5-18 days following recanalization, which corresponds to the period needed for growth factor release from platelets to terminate and which varies among patients. The continuous readministration of photosensitizer serves to replace previously administered photosensitizer, which is cleared from the cells over time, to ensure that the growth factor binding sites are blocked until growth factor has cleared from the tissues. After the majority of the photosensitizing agent has been delivered to the surrounding smooth muscle cells from the VAST but before it clears from the atherosclerotic smooth muscle cells and plaque, the photosensitizing agent is exposed to light at a wavelength at which the photosensitizer absorbs the light causing cell lysis. Since the growth factor has cleared before atherosclerotic plaque and cell lysis, the likelihood of restenosis is significantly reduced or eliminated. The process of activating a photosensitizer with light to cause cell necrosis is called photodynamic therapy, or more particularly in the case of atherosclerosis, photoatherolytic therapy.

The advantages of the medicament dispensing stent over prior art include:

1. Bioabsorbable polymer;
2. Non-thrombogenic;
3. May be a coated metallic stent for reduced thrombogenicity;
4. Localized drug delivery—continuous localized time release drug delivery to affected area eliminates photosensitivity problems which arise following systemic delivery;
5. Maintain structural integrity of vessel (scaffolding);
6. Maintain patency—prevent elastic recoil;
7. Eliminate the need for serial injection of medicament;
8. Eliminate the need for serial oral administration of medicament;
9. Lower systemic doses and higher local doses of medicament;
10. Combined drug therapy (anti-proliferation, anti-recoil, anti-thrombogenicity, anti-platelet, anti-fibrin, anti-collagen); and
11. Combined drug/device therapy.

In summary, the above treatment has the potential to greatly impact the treatment of cardiovascular disease by treating the disease from a cellular cause level (the atherogenesis perspective) and not merely from the conventional palliative approach.

Although the most important application of this novel method is to prevent restenosis following angioplasty or atherectomy of coronary arteries, this technique also can be applied to atherosclerotic arteries located elsewhere, such as the renal, iliac, femoral and popliteal arteries. Additionally, a vaso-absorbable stent can be used to prevent arterial occlusion after coronary by-pass surgery wherein vascular segments are replaced with prosthetic or natural grafts and growth factor is released in response to the arterial wall injury.

The above is a brief description of some deficiencies in the prior art and advantages of the present invention. Other features, advantages and embodiments of the invention will be apparent to those skilled in the art from the following description, accompanying drawings and appended claims.

BRIEF DESCRIPTION OF THE DRAWINGS

FIG. 1 depicts a stent in its non-expanded state.

FIG. 3 (a,b) depicts the same artery as FIG. 2(a-c), but with views before and after an atherectomy procedure has been performed to removed the atheromatous plaque.

FIG. 4 depicts the stent loaded over and angioplasty balloon in a non-expanded state at the lesion site post atherectomy.

FIG. 5 depicts the stent expanded over the expanded angioplasty balloon at the lesion site post atherectomy.

FIG. 6 depicts the stent deployed in the artery post atherectomy where it remains until it is absorbed by the artery wall thus locally delivering a cocktail of medicament continuously to the arterial wall.

DESCRIPTION OF THE PREFERRED EMBODIMENT

Figure 2:
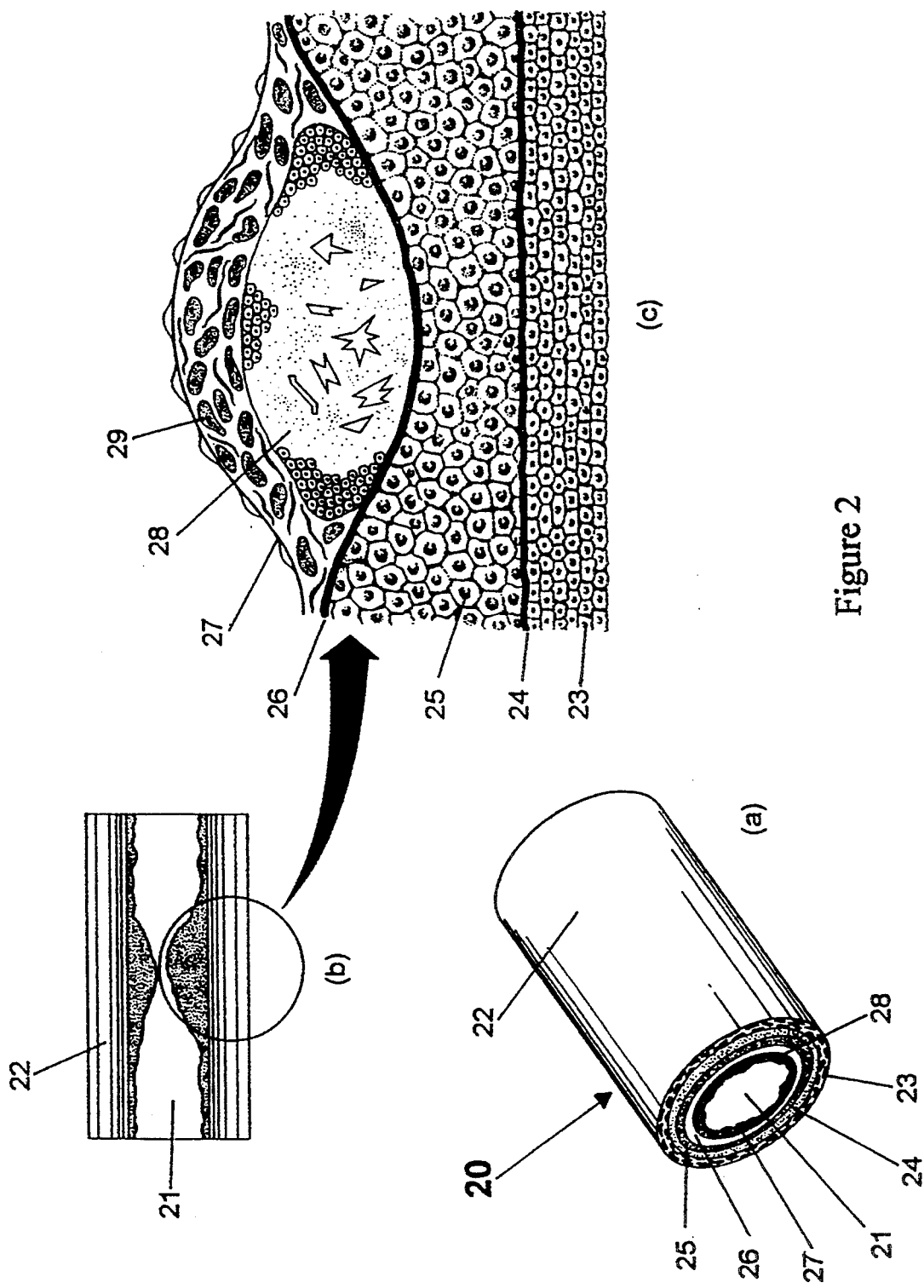
FIG. 2 (a,b,c) depicts an artery with an atheromatous plaque.

According the present invention, photodynamic therapy is used as an adjunctive procedure to primary atherosclerotic treatment, such as percutaneous transluminal coronary angioplasty, laser angioplasty, and atherectomy to minimize or eliminate the occurrence of restenosis. Photodynamic therapy is more appropriately called photoatherolytic therapy (light induced atheromatous SMC lysis) in the specific case of cardiovascular disease.

Photodynamic therapy involves the administration of a particular medicament called a photosensitizer, usually by intravenous injection into an atherosclerotic patient. The photosensitizer, when administered intravenously, is selectively retained by the atheromatous smooth muscle cells and plaque, with little or no retention into healthy areas of the arterial wall. Generally, the photosensitizer is nontoxic to all cells when administered, but once activated by a therapeutic dose of light commonly delivered by a laser at a specific wavelength, the photosensitizer, which has been selectively absorbed in the atherosclerotic cells, becomes toxic. In this way, the activated photosensitizer facilitates the destruction and reabsorption of the host atheromatous plaque and smooth muscle cells (cell necrosis). The mechanism of cell necrosis induced by photodynamic therapy is believed to involve a photochemical reaction that produces a species of oxygen called singlet oxygen, which induces cell death.

Since the surrounding healthy tissue does not retain the photosensitizer to the extent the diseased tissue does, the therapeutic dose of light is benign to the healthy tissue regions resulting in selective necrosis. This process is disclosed using Hematoporphyrin Derivative (HPD) as the photosensitizer in U.S. Pat. No. 4,512,762, to Spears, the disclosure of which is hereby incorporated herein by reference.

According to the present invention, the photosensitizer is administered in such a way as to inhibit smooth muscle cell proliferation following recanalization. It has been found that photosensitizers that have accumulated in smooth muscle cells act in the manner of a competitive inhibitor to block the growth factor binding site, thus preventing the smooth muscle cells from getting "switched on" by growth factor, which would otherwise cause rapid cell proliferation. However, since proliferation of smooth muscle cells occurs immediately or at any time up to several hours after vessel wall injury and continues for about 5 to 18 days (depending on the individual), the timing of the administration of the photosensitizer is critical to the present invention. The effect of the timing of the photosensitizer administration is discussed in detail below.

Growth factor is released in response to arterial wall injury as a result of the primary treatment (e.g., angioplasty). Since release of growth factor continues for about 5–18 days after arterial wall injury, the ubiquitous growth factors are free to "switch on" the remaining smooth muscle cells, resulting in rapid smooth muscle cell proliferation and restenosis. Thus, although concurrent or sequential recanalization with coronary angioplasty (or other interventional therapy) and photodynamic therapy (using a single administration of photosensitizer) reduces the initial proliferation of smooth muscle cells, in the long term such treatment may not be effective.

According to the present invention the preferred method of administering photosensitizer and providing adjunct therapy to cardiovascular intervention is by means of a vaso-absorbable, medicament dispensing stent. Turning now to the drawings, the "base material" of the stent 10 shown in FIG. 1 is preferably a polymer which has the characteristic of being absorbed by the vessel within 30–180 days. Suitable polymers or copolymers include polyglycotic/polylactic acid (PGLA), polycaprolacone (PCL), polyhydroxybutyrate valerate (PHBV) and the like. Since this therapy requires a series of pharmaceuticals to be delivered at specific times, the VAST device 10 is preferably produced in layers, each layer dispensing photosensitizer concentrations to maintain the required levels in adjacent atheromatous tissue. The stent 10 can also be made from stainless steel, titanium, NITINOL, or a variety of other metals. The drugs can be deposited on the metallic stent in a coating layer. The thickness of the drug layer 12 will depend on the time interval in which the drug is desired to be delivered (e.g. 30 days).

If the VAST 10 is made from a bio-absorbable polymer 11, the photosensitive medicament 12 will be impregnated throughout the VAST device to maintain the therapeutic levels during disintegration of the polymer. Photosensitive medicament acts as an inhibitor of smooth muscle cell (SMC) proliferation following vascular injury while also mediating SMC lysis when activated with light energy. One such photosensitive medicament is Tin Ethyl Etiopurpurin (SnET2). SnET2 has been shown to be selectively retained by atheromatous plaques. Table 1 is a list of potentially useful photosensitive medicaments.

Preferably, an anti-platelet/anti-thrombus drug such Heparin, Hirudin, tPA, Streptokinase, Urokinase, Persantine, Aspirin, etc. impregnates the VAST. Since restenosis is a response to injury, platelets are deposited at the lesion site. Platelets, along with other cellular components, release growth factors such as Platelet Derived Growth Factor (PDGF) which activates SMC proliferation. Reducing the number of platelets which get deposited at the site of injury and reducing the incidence of thrombus at the lesion site will greatly enhance the procedure. Thrombus has been associated with abrupt reclosure, embolism and the genesis of intravascular matrix which later becomes fibrous in advanced lesions.

After approximately 14 days, the SMC proliferation is replaced by the aggregation of fibrin and collagen as the dominant event in restenosis. An anti-collagen/anti-fibrin drug such as Heparin is staged to be released after about 14 days.

By taking this combined pharmacological regime, the proliferative events can be prevented while the normal healing process occurs. Once the healing has occurred and the growth factors have cleared from the lesion site, the light activation of the photosensitizer can occur if necessary.

Clinical Method: A patient presents himself/herself to the cardiac catheterization laboratory with a 90% stenosis in the mid left anterior descending (LAD) coronary artery. It is decided that the patient will be treated with an atherectomy procedure to remove a large portion of the obstruction followed by Photoatherolytic (PAL) Therapy to prevent restenosis.

The diseased artery is shown in FIGS. 2a–c. The diseased artery, a segment of which is shown at 20 in FIG. 2a, has an at least partially open central lumen 21 and an arterial wall 22. The wall 22 is comprised of concentric layers of tissue. The outermost layer is the adventitia 23. The external elastic lamina 24 separates the adventitia 23 from the media 25. The internal elastic lamina 26 forms the boundary between the media 25 and the intima 27. The segment of diseased vessel 20 is shown in the longitudinal cross section in FIG. 2(b). The occluded portion comprising the atherosclerotic plaque is enlarged and shown in greater detail in FIG. 2(c). The atheroma consists of a necrotic core 28 surrounded by a layer of smooth muscle cells 29.

The patient is prepared per normal angioplasty procedures including the proper level of anti-coagulation prior to the atherectomy procedure. Turning now to FIG. 3, the atheroma 31 is removed according to standard procedures. Following the atherectomy procedure the majority of the atheroma 31 (FIG. 3(a)) has been removed as shown at 32 in FIG. 3(b) leaving only a small amount of residual atheromatous tissue.

Figure 7:
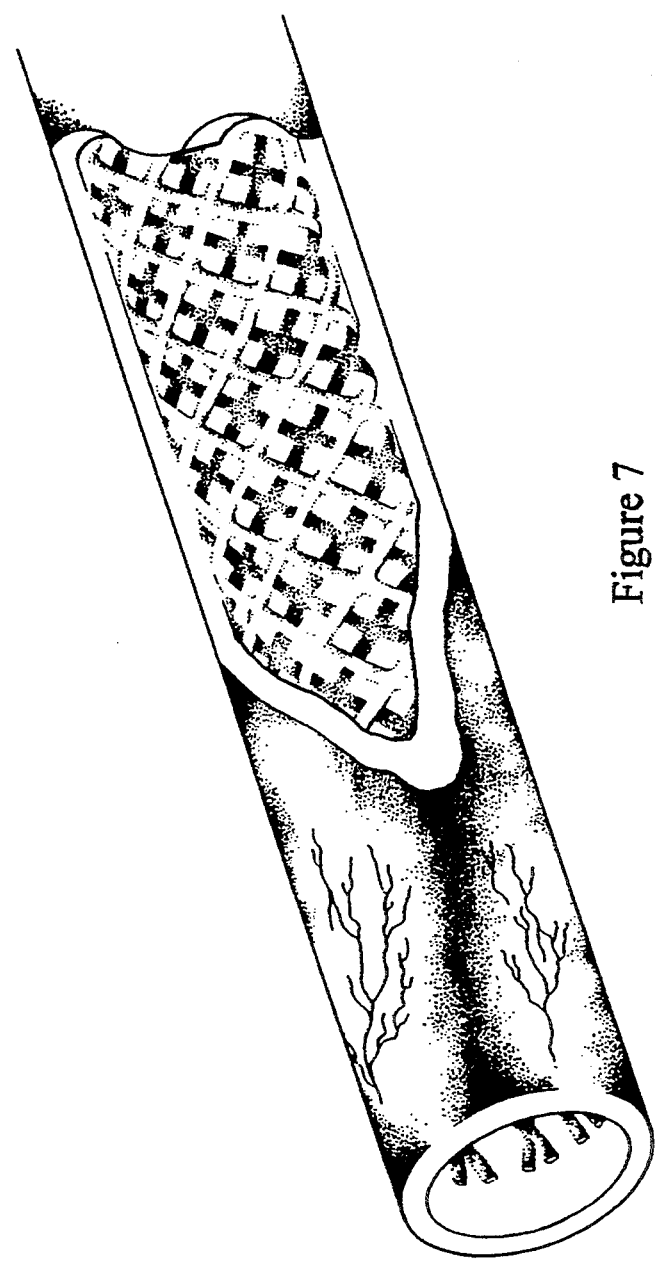
FIG. 7 is a partially cutaway perspective view of the stent deployed in an artery.

Following atherectomy as outlined above, the VAST device 10 is introduced into the vessel over a standard angioplasty balloon catheter 42 as shown in FIG. 4. Once at the site of the lesion the VAST 10 is deployed by inflating the balloon portion 42 of the catheter 41 as shown in FIG. 5. The balloon catheter 42 is then removed leaving the VAST in place as shown in FIGS. 6 and 7. The patient is then allowed to recover as with a standard atherectomy procedure. Since the VAST contains Heparin or another anti-coagulant, heavy anti-coagulation is not required as with the placement of standard metallic stents. It is advisable to prescribe an aspirin per day for the duration of the therapy. During that time the VAST releases the cocktail of therapeutic agents to the residual atheromatous lesion in a time release fashion.

Approximately 30 days following placement of the VAST, the patient presents to the cardiac cath lab. A sample of the patient's blood is taken and tested for levels of photosensitizer, anti-coagulant/anti-thrombus agent and anti-collagen/anti-fibrin agent. The level of photosensitizer (PS) is observed closely to determine if a systemic injection of the PS is required to effectively perform the Photodynamic Therapy (PDT) part of the procedure. If additional PS is required, the typical delay time for optimum photosensitization (i.e., 24 hours) must be observed.

If smooth muscle cell proliferation is controlled early enough and control maintained until growth factors clears, and if the arterial lumen is sufficiently widened, the light activation therapy may not be necessary, making this solely a pharmacokinetic therapy.

Photosensitizers which may be dispensed by the stent according to this invention include the following classes: purpurins, verdins, chlorins, phthalocyanines, phorbides, bacteriochlorophylls, porphyrins, chalcogenapyryliums, texaphyrins, xanthenes, benzophenoxasines, phenohiazines, di- and triaylmethanes, and kryptocyanines. Preferred members of the above classes are listed in the following table. The optimum light wavelength for activating each member to achieve necrosis is provided in the right column.

TABLE 1

| CLASS | PREFERRED COMPOUND | ACTIVATION Wavelength (nm) |
|---|---|---|
| Purpurins (metalized) | Tin Ethyl Etiopurpurin | 660 |
| Purpurins (non-metalized) | Ethyl Etiopurpurin | 695 |
| Verdins | Coproverdin-II-Tripotassium Salt | 700 |
| Chlorins | Octaethyl | 650 |
| Phthalocyanines | Chloaluminum Sulfonated Phthyalocyanine | 665 |
| Phorbides | Mono-L-Aspoartyl Chlorin e6 | 660 |
| Bacteriochlorophylls | Bacterochlorophyll-a | 780 |
| Porphyrins | Protoporphyrin-IX | 630 |
| Chalcogenapyryliums | Chalcogenapyrylium 8b | 800 |
| Texaphyrines | Texaphyrin | 780 |
| Xanthenes | Rhodamine 123 | 480–520 |
| Benzophenoxazines | Nile Blue | 680 |
| Phenothiazines | Methylene Blue | 660 |
| Di and Triayl Methanes | Victoria Blue-BO | 660 |
| Kryptocyanines | EDKC* | 660–700 |

*EDKC = N,N-bis[2 ethyl-1, 3-dioxolane] kryptocyanine

The preferred photosensitizing agent is Tin Ethyl Eitopurpurin having the chemical name: Ethyl 3,4,20,21-tetradehydro-4,9,14,19-tetraethyl-18,19-dihydro-3,8,13,18-tetramethyl-20-phorbine carboxylato(2-)-$N^{23}$, $N^{24}$, $N^{25}$, $N^{26}$-tin(IV) dichloride. It has been found that there is little or no retention of this drug in the skin, thereby avoiding problems that can result from exposure of the patient to ordinary sunlight (i. e., activation of the photosensitizer in the skin). In addition, Tin Ethyl Etiopurpurin has a high therapeutic ratio (concentration level in diseased tissue relative to healthy tissue) as compared to other photosensitizers such as hematoporphyrin derivative (HPD). Tin Ethyl Etiopurpurin also is advantageously activated at longer wavelengths (660–690 nanometers). At these wavelengths, the light is attenuated to a much lesser degree by the blood as is the case with 630 nanometer wavelength light (the optimum wavelength for HPD, for example). As a result of using a longer activation wavelength, a substantially greater amount of light gets to the vessel wall and photosensitizer, thereby increasing procedure efficiencies.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What I claim is:

1. An intravascular stent having a medicament containing portion which disintegrates following implantation within a blood vessel and wherein the disintegration of said medicament containing portion is operable for the contemporaneous release of medicament from said medicament containing portion of said stent and wherein the medicament is a smooth muscle cell proliferation inhibitor which is substantially completely released from said medicament containing portion within 15 days following implantation of said stent within the blood vessel.

* * * * *